United States Patent
Taheri

[19]

[11] Patent Number: 6,120,524
[45] Date of Patent: Sep. 19, 2000

[54] DEVICE FOR CLOSING AN ARTERIAL PUNCTURE AND METHOD

[76] Inventor: Syde A. Taheri, 1275 Delaware Ave., Buffalo, N.Y. 14209

[21] Appl. No.: 09/283,934

[22] Filed: Apr. 1, 1999

Related U.S. Application Data

[60] Provisional application No. 60/120,165, Feb. 16, 1999, abandoned.

[51] Int. Cl.[7] .................................................. A61B 17/08
[52] U.S. Cl. .......................................... 606/213; 606/153
[58] Field of Search .................................. 606/213, 215, 606/153, 155, 157, 151, 139

[56] References Cited

U.S. PATENT DOCUMENTS

| | | | |
|---|---|---|---|
| 4,259,959 | 4/1981 | Walker | 128/337 |
| 5,254,127 | 10/1993 | Wholey | 606/153 |
| 5,383,897 | 1/1995 | Wholey | 606/213 |
| 5,634,936 | 6/1997 | Linden et al. | 606/213 |

*Primary Examiner*—Michael Buiz
*Assistant Examiner*—Kevin Truong
*Attorney, Agent, or Firm*—Hodgson Russ Andrews Woods & Goodyear LLP

[57] ABSTRACT

A patch that is deployed inside an artery and the like to close a puncture in the artery, is described. The patch includes an enclosing support having a sheet of microporous material secured to a perimeter thereof and at least two protrusions extending from the support. The patch is deployed inside the artery and then pulled up against the artery wall by strings connected to the patch to thereby seal the puncture.

20 Claims, 7 Drawing Sheets

DEVICE FOR CLOSING AN ARTERIAL PUNCTURE AND METHOD

CROSS-REFERENCE TO RELATED APPLICATION

The present application claims priority based on U.S. provisional application Ser. No. 60/120,165, filed Feb. 16, 1999 now abn.

BACKGROUND OF THE INVENTION

1. Field of the Invention

The present invention generally relates to a device for closing a puncture, and method of effecting the closure. More particularly, the present invention relates to closing an opening in an artery.

2. Prior Art

There are approximately 5 million angiographs performed in the United States each year. Over one hundred thousand of these cases require surgical intervention to close the arterial puncture resulting from the angiograph. This large number of interventions means that existing techniques are associated with high incidences of failure. Accordingly, there is a need for a device and method for closing a puncture to seal the same, and particularly, a device and method for closing an arterial puncture and the like.

SUMMARY OF THE INVENTION

The present invention is directed to a patch that is deployed inside an artery and the like to close and seal a puncture in the artery. The patch includes an enclosing support having a sheet or cloth of microporous material secured to the perimeter thereof. The enclosing support is larger than the puncture and has at least two spaced apart protrusions extending therefrom. The patch is deployed inside the artery and then pulled up against the artery wall by strings attached to the patch. As this happens, the protrusions pierce the artery wall to anchor the patch in place, closing the puncture. The strings are then cut or allowed to degrade on their own.

These and other aspects of the present invention will become increasingly more apparent to those skilled in the art by reference to the following description and to the appended drawings.

DESCRIPTION OF THE PREFERRED EMBODIMENTS

Figure 1:
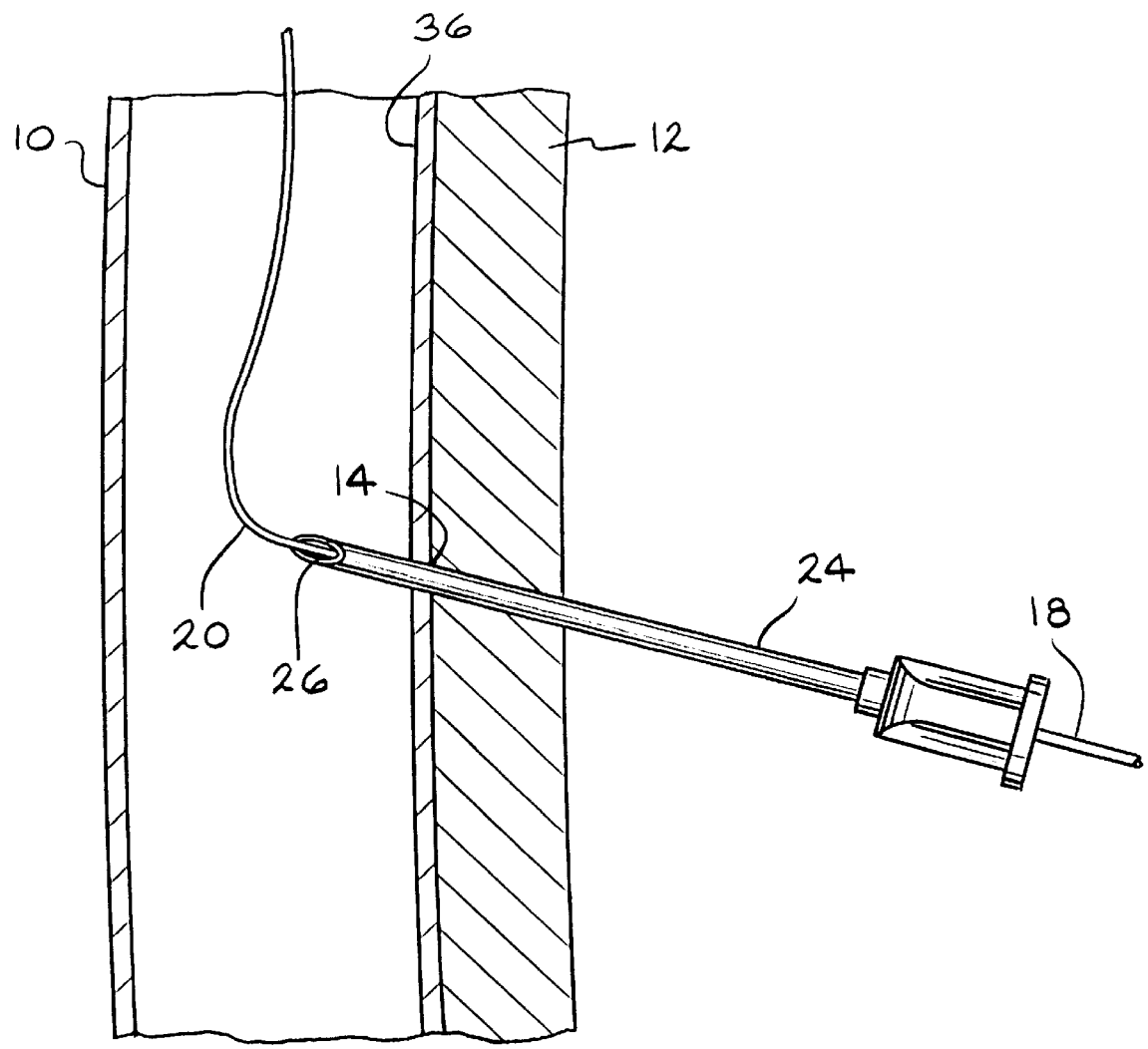
FIG. 1 is an enlarged perspective view of a catheter 24 received over a guide wire 18 extending through a puncture 14 in an artery 10.
Figure 2:
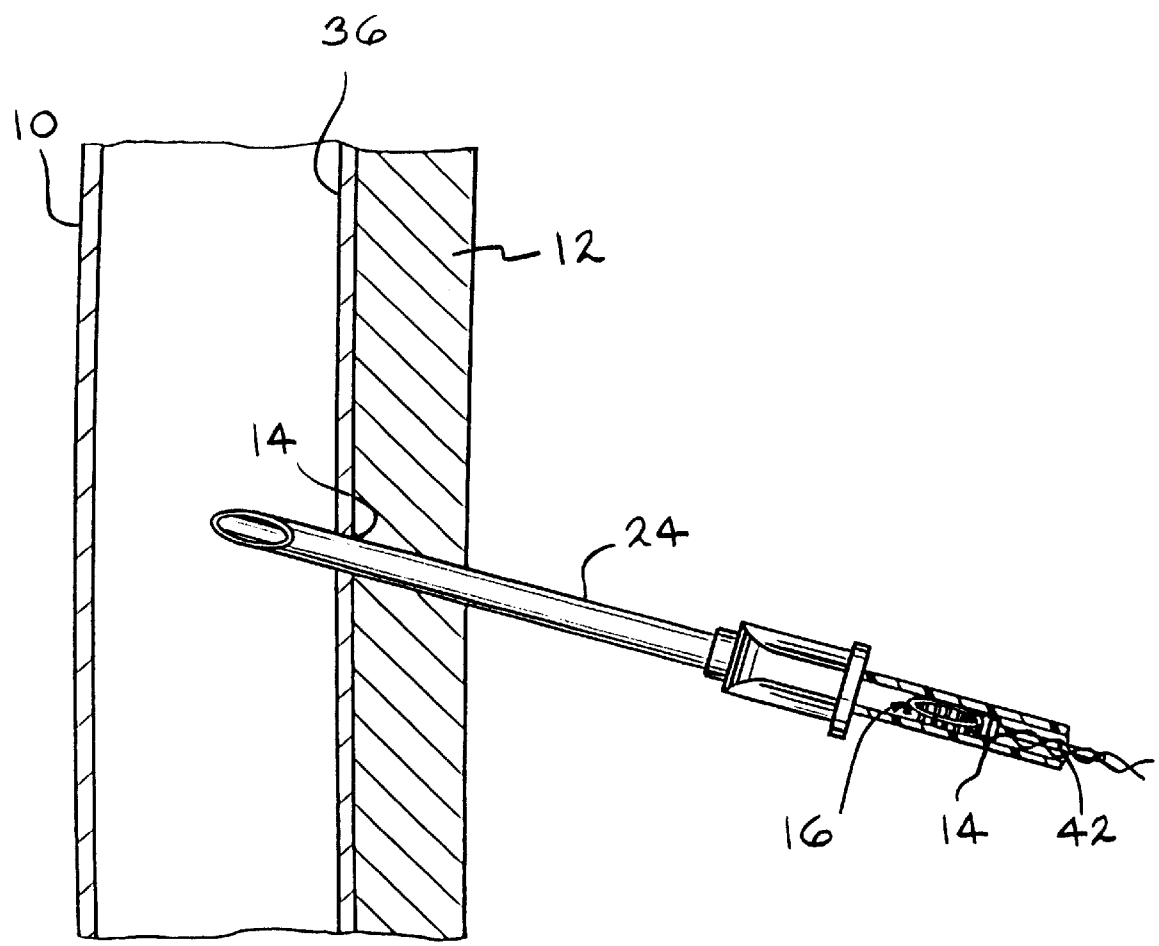
FIG. 2 is a perspective view of a patch 16 according to the present invention being moved through the catheter 24.
Figure 3:
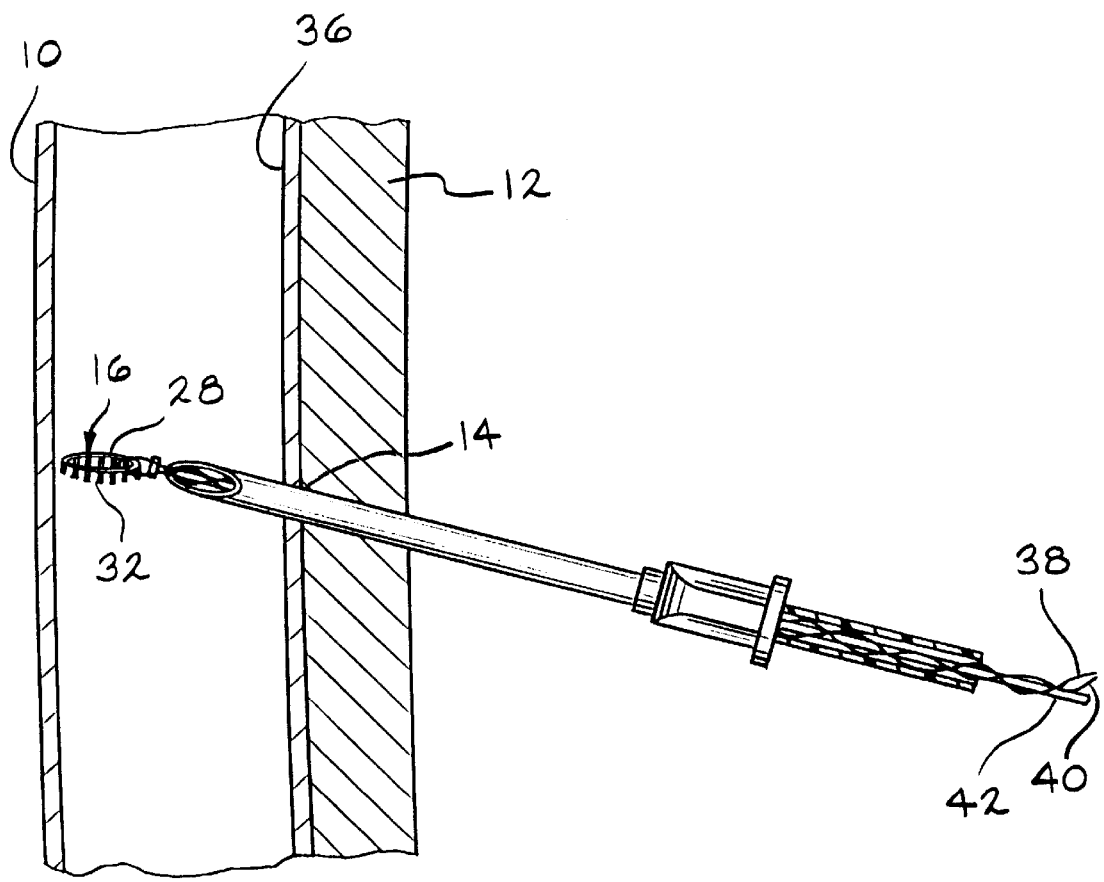
FIG. 3 is a perspective view of the patch 16 partially deployed out the distal open end of the catheter 24.

Referring now to the drawings, FIG. 1 shows an artery 10 proximate a muscle 12, such as a cardiac muscle and the like. The artery 10 possesses a puncture opening 14 as a result of a surgical procedure, such as an angiograph and the like. According to the present invention, the puncture is sealed in a safe and efficient manner by a patch 16 (FIGS. 2 to 7) serving as a closure device for the puncture 14.

In order to provide the patch 16 closing the puncture 14, a needle (not shown) is moved through the puncture 14 to position a distal end of the needle in the artery 10. The needle is of a metallic material that is compatible with the physiology of the host body and is readily detectable by conventional imaging means. In that manner, the precise position of the needle is determined by imaging its location until the needle is properly positioned in the artery 10.

The needle serves as a lumen for placement of a guide wire 18 through the muscle 12 and through the puncture opening 14 so that a distal portion 20 of the wire resides in the artery lumen 22. The guide wire 18 serves to direct the placement of various surgical instruments to perform a medical procedure such as an angiograph and the like.

After completion of the angiograph, the guide wire 18 is left inside the artery lumen 22 extending through the puncture 14. As shown in FIG. 1, a double lumen catheter 24 is then moved along the guide wire 18 until a distal open end 26 thereof is positioned in the artery, adjacent to the puncture 14. The guide wire 18 is then removed from the artery and the catheter 24.

As shown in FIGS. 2 to 7, a self-expanding wire loop 28, such as a Nitinol wire, provides an enclosing support. The enclosing support 28 has a thin wall sheet or cloth of a microporous material 30 (FIG. 6) secured to the perimeter thereof. In a preferred embodiment of the present invention, the wire support 28 is readily foldable into a shape that is movable through the lumen of the catheter, and the sheet 30 is of a polyurethane material sewn or otherwise secured to the perimeter of the support 28. In another embodiment of the present invention, the catheter 24 serves to dilate the puncture opening 14 to a size sufficient to have the catheter 24 provided with a lumen that enables the enclosing support 28 to move therethrough in an unfolded condition. At such time as the catheter 24 is removed from the puncture 14, the opening in the artery closes somewhat to a size that is smaller than the perimeter of the support 28. This is especially the case if the wire support 28 is moved through the catheter unfolded. If the wire support is deployed in a folded condition and subsequently unfolded once it has left the catheter, rebound of the artery tissue surrounding the opening is not as critical. In any event, the deployed patch 16 including the enclosing support 28 must be larger than the opening.

Figure 4:
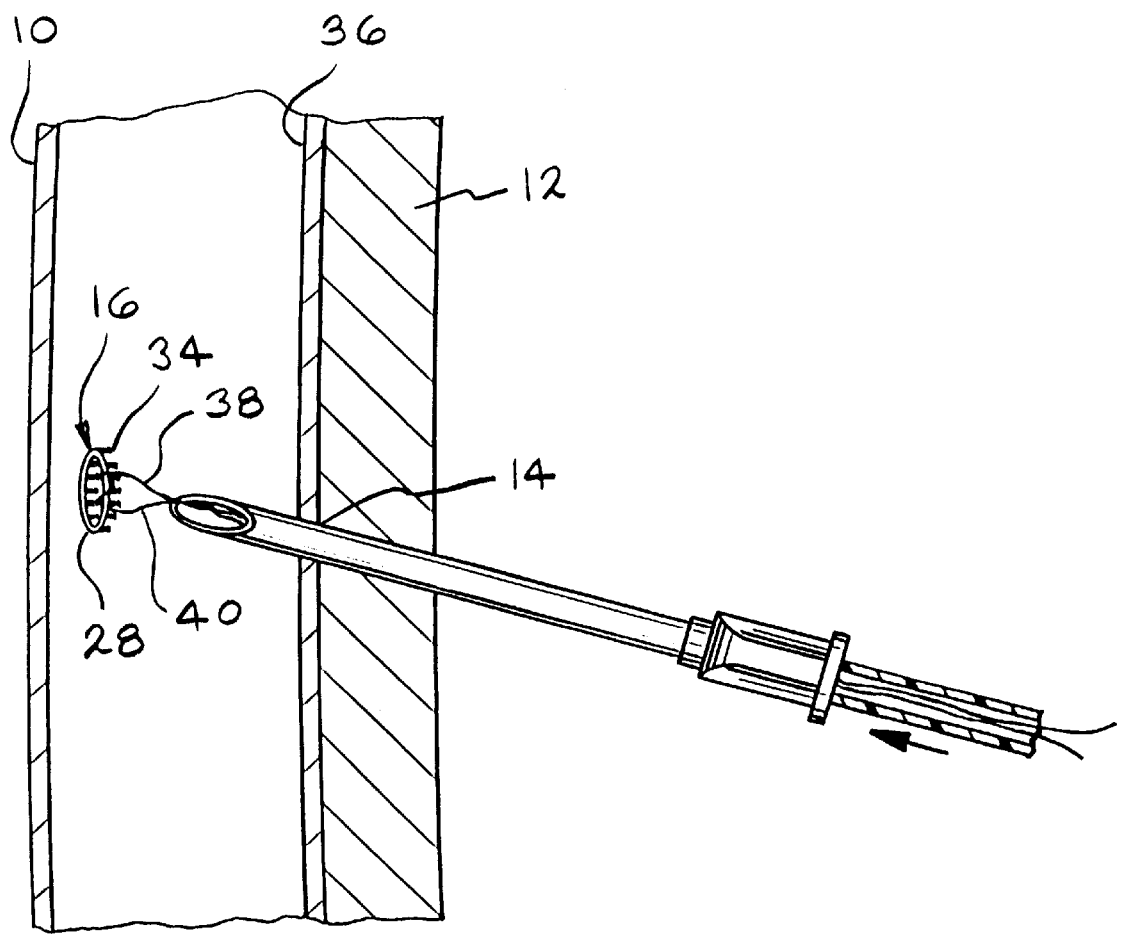
FIG. 4 is a perspective view of the patch 16 fully deployed out the distal open end of the catheter 24.
Figure 6:
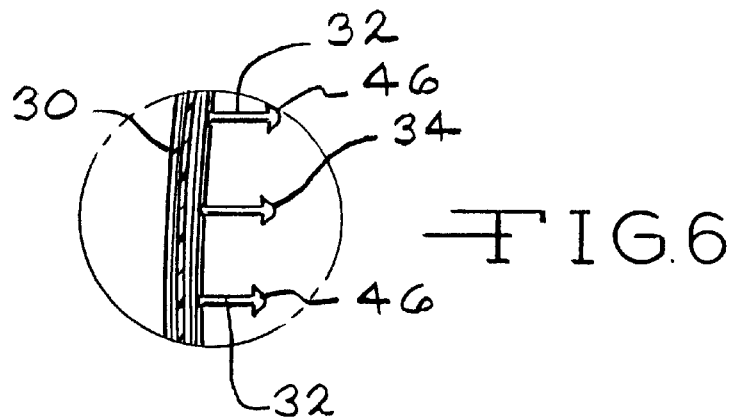
FIG. 6 is an enlarged view of the indicated portion of FIG. 5.
Figure 5:
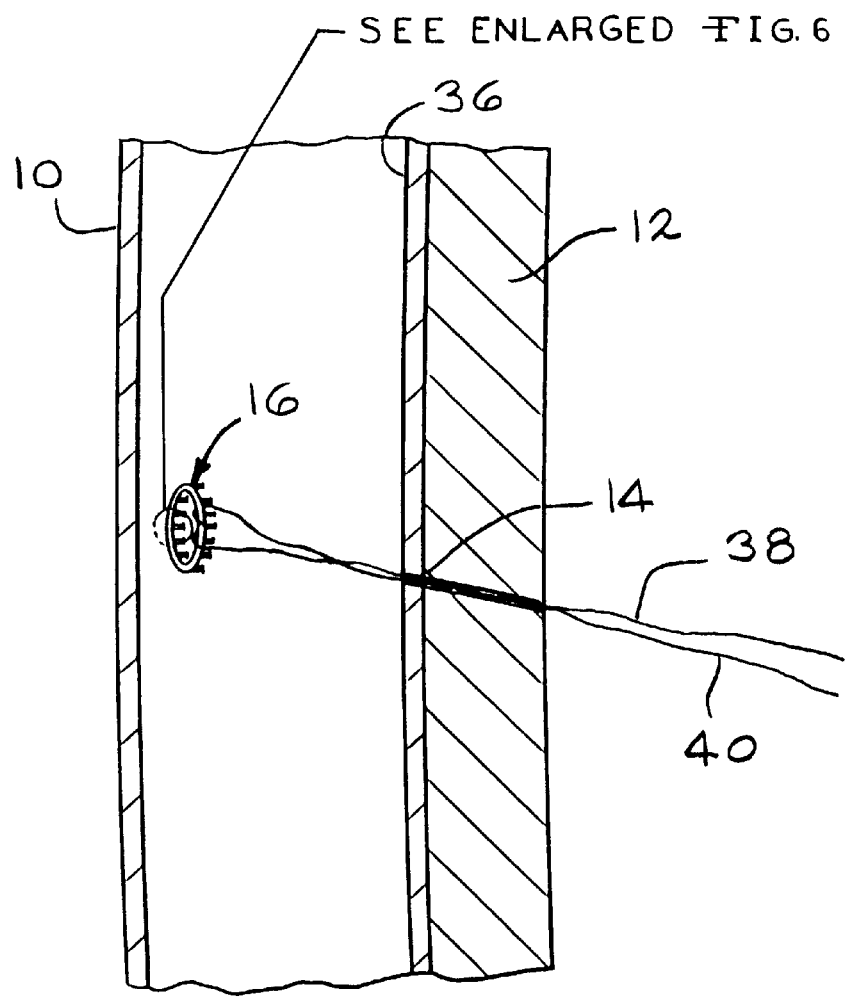
FIG. 5 is a perspective view of the patch 16 just before it is moved into position to seal the puncture 14 in the artery 10.
Figure 7:
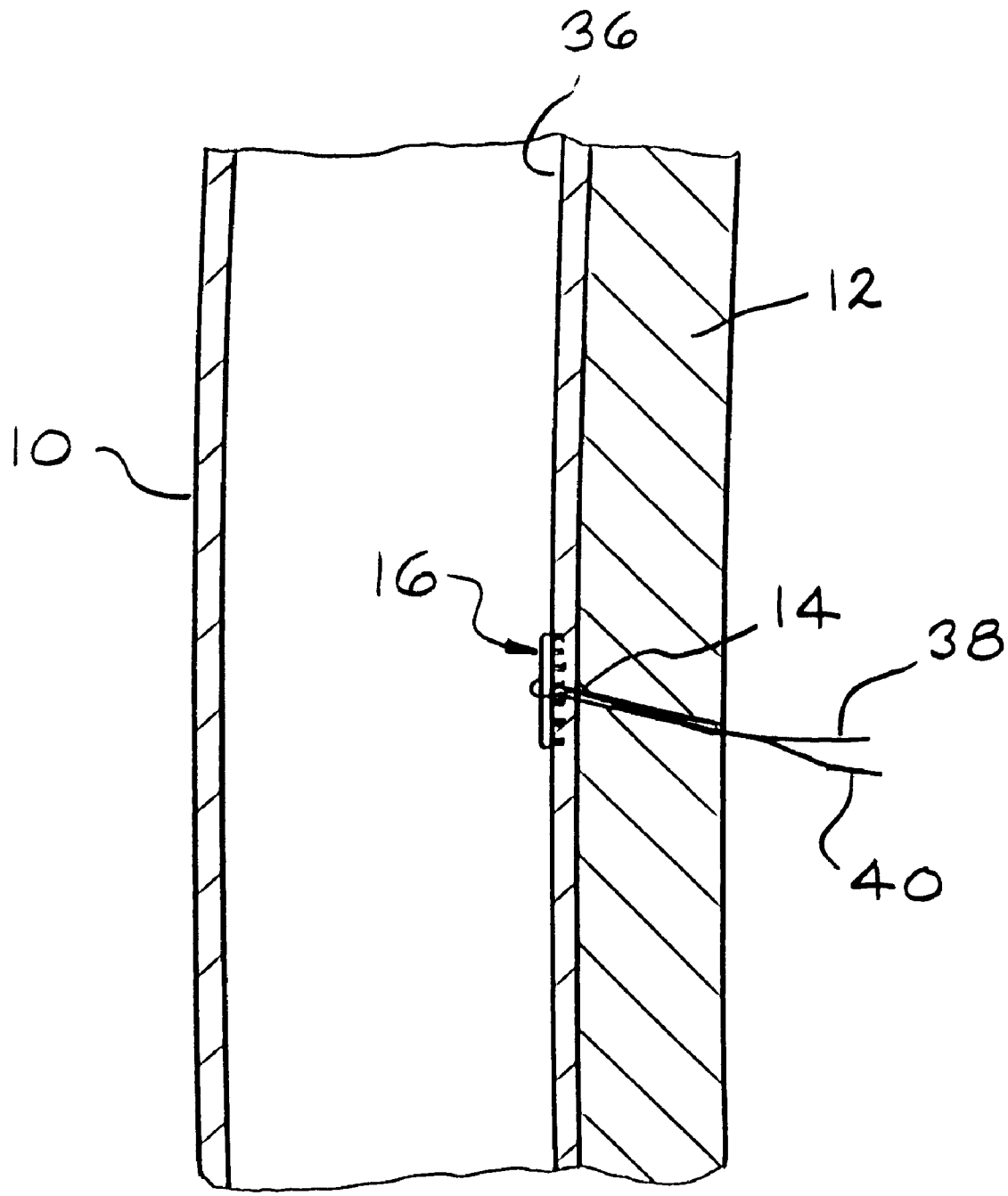
FIG. 7 is a perspective view of the patch 16 closing the puncture 14.

The enclosing support 28 is provided with a plurality of protrusions 32 spaced about the perimeter thereof. The protrusions 32 are in the form of staples or wire-like projections that extend from the support. As shown in FIG. 4, just prior to closing the puncture the distal ends 34 of the protrusions point toward the inner side 36 of the artery 22. With this construction, the protrusions 32 do not extend outwardly beyond the radial perimeter of the support, nor do they extend inwardly to interfere with an enclosed projection of the area bounded by the support 28. In a broader sense, however, the wire support 28 can be of any shape as long as it forms an enclosure and the projections extend from a side of the enclosing structure to neither extend outwardly or inwardly with respect to a projection of the thickness of the enclosing support.

As shown in FIG. 4, the enclosing support 28 is further provided with a pair of spaced apart strings 38 and 40 connected to opposed portions of the support. The strings are preferably of a degradable material that is safe to the host body. In an alternate embodiment, the strings are connected to spaced apart ones of the protrusions 32. In a preferred embodiment of the present invention, the strings 38, 40 are coded, such as by color, to indicate the relative position of the enclosing support 28 and its protrusions 32 inside the artery lumen 22 and, later, when the patch seals the puncture 14. In still a further embodiment, there is only one string that bifurcates proximate the enclosing support to connect to spaced apart portions of the support or to spaced apart protrusions.

To seal the puncture, the patch 16 connected to the strings 38, 40 is moved through the catheter and out a distal open end thereof by a push rod 42 provided with a distal pusher plate 44. Accordingly, after the patch 16 is deployed out the distal open end 26 of the catheter 24, the catheter is removed from the puncture 14 in the artery and the strings 38, 40 are pulled to move the patch 16 comprising the support 28 and covering sheet 30 up against the inner side 36 of the artery 22. The strings 38, 40 are further pulled to cause the protrusions to pierce the artery wall 22 surrounding the puncture 14 with the protrusions seating in the wall. The protrusions are preferably provided with barbs 46 that serve to anchor the patch 16 in place. Accordingly, the enclosing support 28 is circular or oval and is of a size sufficient to surround the puncture 14 to close it with the microporous material 30. The support, being flexible, also readily conforms to the non-planar shape of the artery to effectively seal against the inner side 36 of the artery surrounding the puncture.

While it is within the scope of the present invention to secure the strings 38, 40 to opposed portions of the enclosing support 28 or to diametrically opposed protrusions 32, it is most preferred to secure the strings to the support. That way, the strings do not interfere with movement of the protrusions through the arterial wall. After the patch 16 is in place closing the puncture, the strings are then temporarily secured to the skin for future removal.

Figure 8:
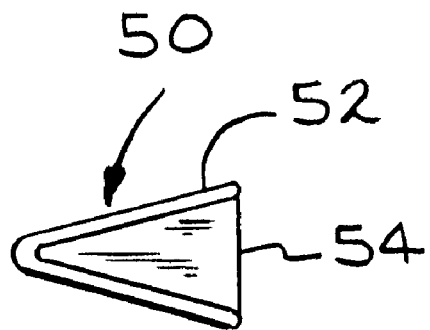
FIGS. 8 and 9 are alternate embodiments of patches 50 and 60 according to the present invention.
Figure 9:
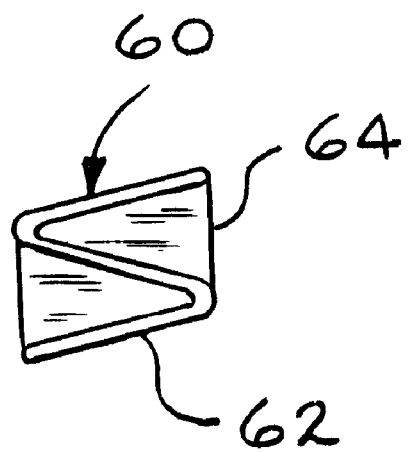

As shown in FIG. 8, it is further contemplated by the scope of the present invention that a closure for an opening or puncture can comprise a patch 50 having a support structure 52 that is not enclosing. In that respect, the support is V-shaped or some other unclosed shape that supports a sheet of microporous material 54. The V-shape is particularly adapted to fit through the lumen of a catheter. Other unenclosed shapes are also contemplated, such as patch 60 shown in FIG. 9 Patch 60 has a support structure 62 that is generally in a Z-shape supporting a sheet of microporous material 64. The views of the patches 50 and 60 do not show their protrusion, however, as previously described, protrusions are an integral and necessary part of the invention. What is required is that the support has a perimeter that substantially seals about the opening to close the puncture in the artery. Further, the support need not be of a wire material, but can be of a thermoplastic material, ceramic or other material. In a broader sense, however, a patch according to the present invention need not even have a support structure separate from the microporous sheet. The patch can be fabricated from a plastic material, for example, and the support, sheet and protrusions can be unitary.

Accordingly, the closure device of the present invention is a new approach for sealing off an arterial vessel that would otherwise require surgical intervention, hospitalization and lengthy intervention.

It is appreciated that various modifications to the inventive concepts described herein may be apparent to those of ordinary skill in the art without departing from the spirit and scope of the present invention as defined by the herein appended claims.

What is claimed is:

1. A patch for closing an opening through body tissue, the patch comprising:
   a) a support structure having a circular shape and provided on an inner side of the body tissue, wherein the support structure is sized to be in a surrounding relationship with the opening;
   b) a sheet of impermeable material secured to a perimeter of the support structure; and
   c) at least two protrusions extending from spaced apart portions of the support structure, wherein the support structure is seated against the inner side of the body tissue with the protrusions extending at least part way through the body tissue so that the sheet of impermeable material closes the opening.

2. The patch of claim 1 wherein the support structure is selected from the group consisting of a wire, thermoplastic material and ceramic material.

3. The patch of claim 1 wherein a distal end of the protrusions is provided with barbs that anchor the support structure to the body tissue.

4. The patch of claim 1 wherein the support structure is of a flexible material that readily conforms to the shape of the inner side of the body tissue.

5. The patch of claim 1 wherein the sheet of impermeable material is of polyurethane.

6. The patch of claim 1 wherein the support structure, sheet and protrusions are unitary.

7. The patch of claim 6 wherein the patch is of a plastic material.

8. A method for providing a patch for closing an opening in a body tissue, comprising the steps of:
   a) providing a catheter extending through the opening in the body tissue with a distal open end of the catheter positioned proximate an inner side of the body tissue;
   b) providing a patch comprising a support structure having a shape selected from a circular shape and a non-circular shape with at least two spaced apart ends, and a sheet of impermeable material secured to the support structure, wherein there are at least two protrusions extending from spaced apart portions of the support structure;
   c) providing at least one string connected to either the support structure or to the protrusions;
   d) moving the patch along a lumen of the catheter and out the distal open end thereof to position the patch proximate the inner side of the body tissue with the protrusions extending toward the body tissue;
   e) moving the catheter so that its distal open end no longer resides proximate the inner side but, instead, resides proximate a near side of the body tissue; and
   f) pulling on the string to cause the patch to move against the inner side of the body tissue with the protrusions embedded in the body tissue and the impermeable material closing the opening in the body tissue.

9. The method of claim 8 including providing this support structure as a wire having a circular shape.

10. The method of claim 8 including providing the support structure having a V-shape.

11. The method of claim 8 including providing the distal end of the protrusions with barbs that anchor the patch to the body tissue.

12. The method of claim 8 including providing the support structure of a flexible material that readily conforms to the shape of the inner side of the body tissue.

13. The method of claim 8 including providing the sheet of impermeable material of polyurethane.

14. The method of claim 8 including providing the support structure in a folded shape as it is moved through the lumen of the catheter.

15. The method of claim 8 including providing the support structure in an unfolded, substantially planar shape as it is moved through the lumen of the catheter.

16. The method of claim 8 including providing at least two string connected to either the support structure or the protrusions.

17. The method of claim 16 including color coding the at least two strings.

18. The method of claim 8 including providing a pusher device that deploys the patch out a distal open end of the catheter in a position generally coaxial with the opening in the body tissue.

19. A patch assembly for closing an opening through body tissue, the patch assembly comprising:
   a) a support structure provided on an inner side of the body tissue, wherein the support structure has a non-circular shape with at least two ends which are spaced apart so as to reside on opposed sides of the opening;
   b) a sheet of impermeable material secured to a perimeter of the support structure; and
   c) at least two protrusions extending from spaced apart portions of the support structure, wherein the support structure is seated against the inner side of the body tissue with the protrusions extending at least part way through the body tissue so that the sheet of impermeable material closes the opening.

20. The patch of claim 19 wherein the support structure is V-shaped.

\* \* \* \* \*